United States Patent [19]
Laboureau et al.

[11] Patent Number: 5,662,655
[45] Date of Patent: Sep. 2, 1997

[54] OSTEOSYNTHESIS PLATE-STAPLE

[76] Inventors: Jacques Philippe Laboureau, 24, rue Fontaine Billenois, Dijon F-21000, France; Gerard H. Dericks, 3087 Noela Dr., Honolulu, Hi. 96815

[21] Appl. No.: 367,321
[22] PCT Filed: Jul. 23, 1993
[86] PCT No.: PCT/FR93/00754
§ 371 Date: Mar. 16, 1995
§ 102(e) Date: Mar. 16, 1995
[87] PCT Pub. No.: WO94/02073
PCT Pub. Date: Feb. 3, 1994

[30] Foreign Application Priority Data

Jul. 24, 1992 [FR] France .................. 92 09149

[51] Int. Cl.⁶ .................................. A61B 17/58
[52] U.S. Cl. .................. 606/75; 606/69; 606/72
[58] Field of Search .................. 606/60, 69, 70, 606/71, 72, 73, 75, 76, 77; 411/457, 470, 920

[56] References Cited

U.S. PATENT DOCUMENTS

| | | | |
|---|---|---|---|
| D. 286,180 | 10/1986 | Korthoff | D24/27 |
| 780,019 | 1/1905 | Arendt | 411/920 |
| 2,155,746 | 4/1939 | Williams | 606/75 |
| 3,552,389 | 1/1971 | Allgower et al. | 606/69 |
| 3,824,995 | 7/1974 | Getscher et al. | 606/69 |
| 4,408,601 | 10/1983 | Wenk | 606/69 |
| 4,493,317 | 1/1985 | Klaue | 606/69 |
| 4,565,193 | 1/1986 | Streli | |
| 4,570,623 | 2/1986 | Ellison et al. | 606/75 |
| 4,592,346 | 6/1986 | Jurguitis | |
| 4,755,091 | 7/1988 | Potucek et al. | 411/920 |
| 4,848,328 | 7/1989 | Laboureau et al. | |
| 4,913,144 | 4/1990 | Del Medico | |
| 5,053,038 | 10/1991 | Sheehan | |
| 5,084,050 | 1/1992 | Draenert | |
| 5,108,399 | 4/1992 | Eitenmuller et al. | 606/77 |
| 5,246,443 | 9/1993 | Mai | 606/72 |

FOREIGN PATENT DOCUMENTS

| | | | |
|---|---|---|---|
| 551875 | 12/1959 | Belgium . | |
| 0354599 | 2/1990 | European Pat. Off. . | |
| 2642641 | 8/1990 | France . | |
| 2668921 | 5/1992 | France . | |
| 2702646 | 9/1994 | France | 606/75 |
| 9423654 | 10/1994 | France | 606/75 |
| 824239 | 12/1951 | Germany . | |
| 3445738 | 6/1986 | Germany . | |
| 597838 | 4/1978 | Switzerland . | |
| 2126903 | 4/1984 | United Kingdom . | |
| 90/00370 | 1/1990 | WIPO . | |

*Primary Examiner*—Michael Buiz
*Assistant Examiner*—Julian W. Woo
*Attorney, Agent, or Firm*—Greenblum & Bernstein P.L.C.

[57] ABSTRACT

Osteosynthesis plate-staple for osteotomy, including symmetrical or asymmetrical side legs having sharpened free ends, and being joined by a cross member. The legs are substantially mutually longitudinal divergent in the direction of their free ends so that the ends are urged away from one another when the staple is implanted, whereby bone fragments on either side of the fracture line are resiliently compressed. Further, asymmetrical side legs have different shapes depending upon whether they are to be inserted into the metaphyseal portion of the bone, or implanted in the cortical bone.

31 Claims, 3 Drawing Sheets

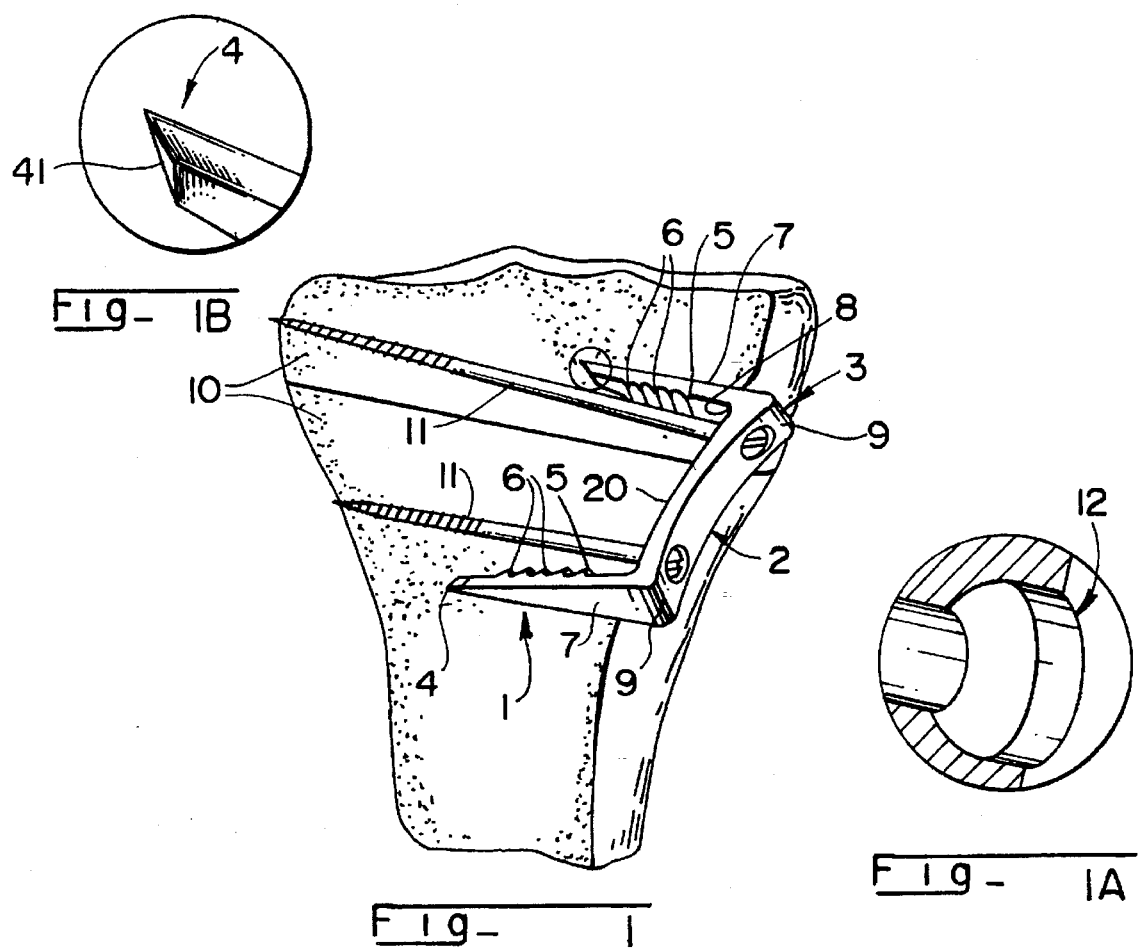
Fig- 1B
Fig- 1
Fig- 1A
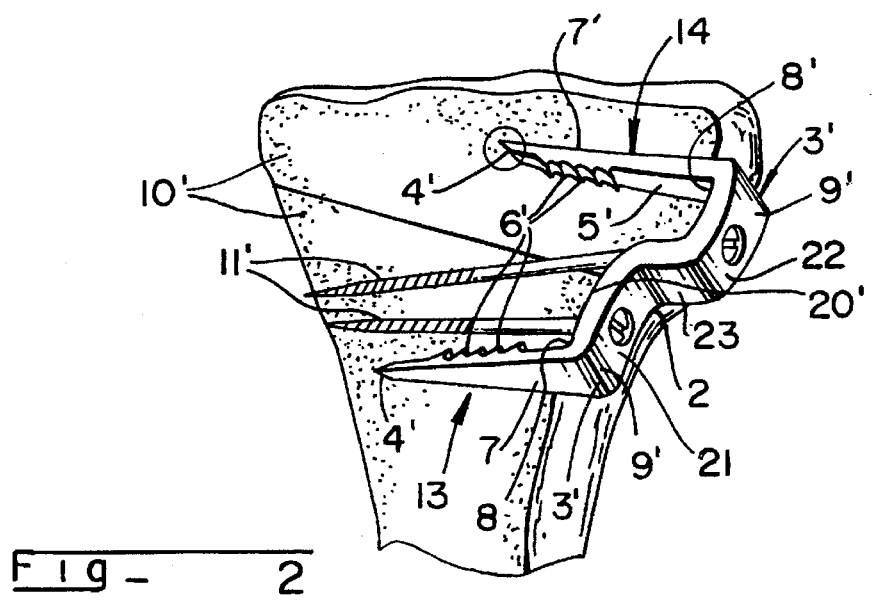
Fig- 2

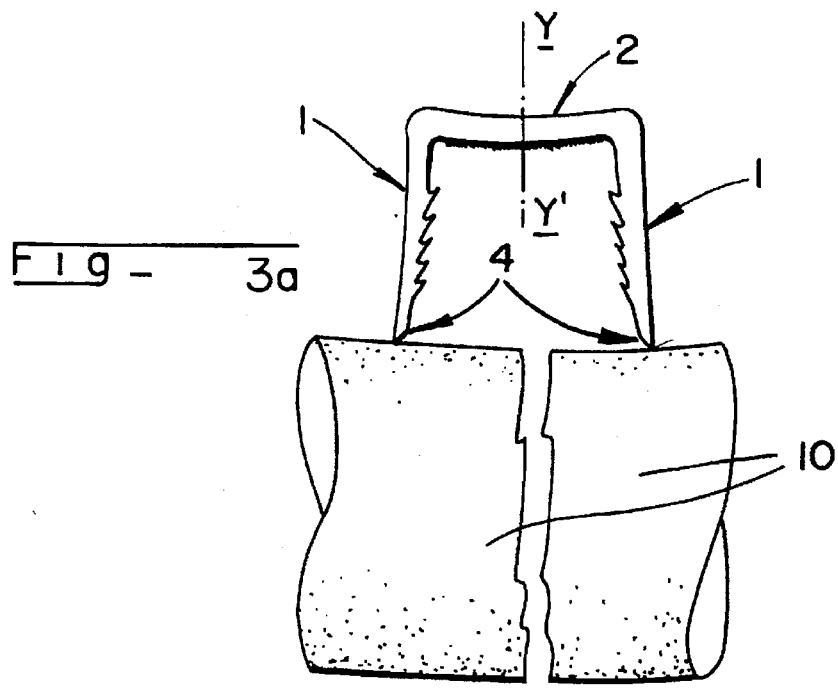
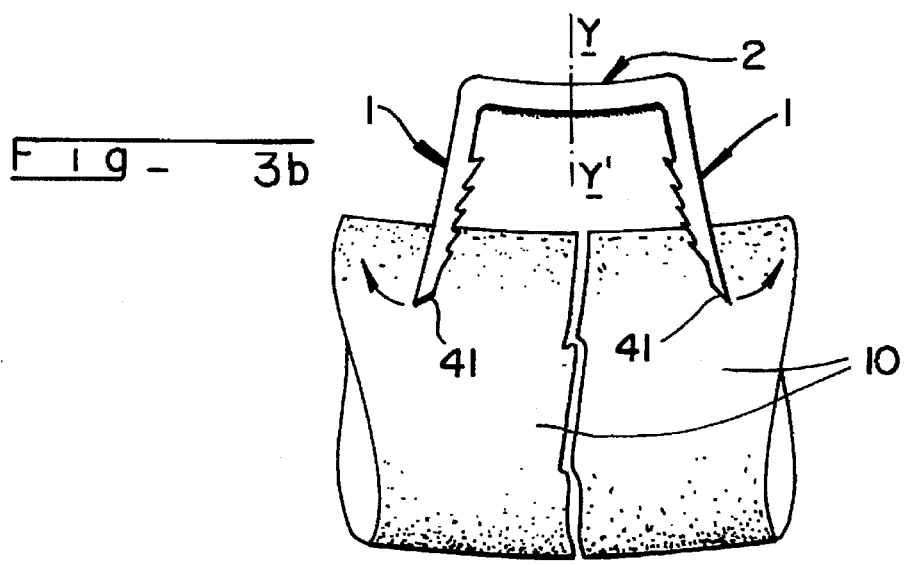
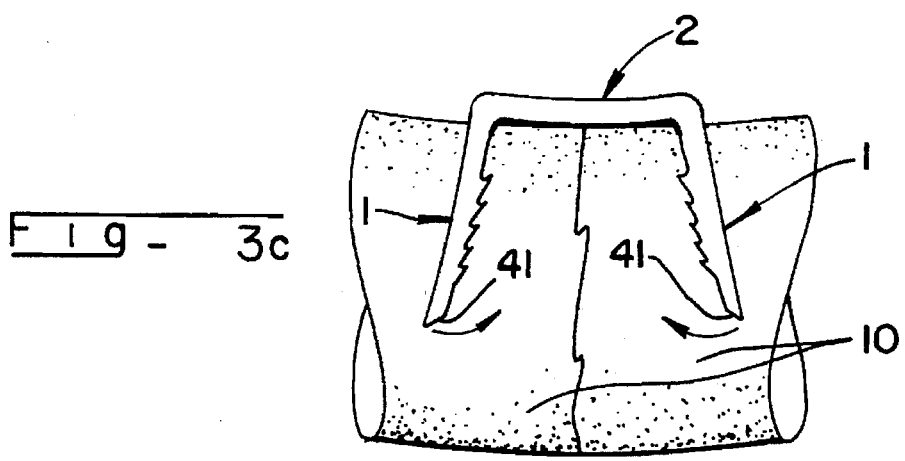

OSTEOSYNTHESIS PLATE-STAPLE

BACKGROUND OF THE INVENTION

1. Field of the Invention

The present invention concerns a new staple that can be easily used both as a staple and as an osteosynthesis plate specifically designed for tibia and femur osteotomies.

2. Discussion of Background Information

FR 2 642 641 describes a surgical staple in the form of a <<U <<, which has two parallel side legs having sharpened free ends and being joined by a cross member. The cross member is pierced by at least one hole approximately parallel to the side legs and intended to take at least one additional fixing device. The side legs of the staple have, firstly, at their end, a sharpened part pointing approximately towards the inside and, secondly, on their external surface a series of teeth, the ridges of which point approximately upwards. The internal part of the cross member between the side legs of the staple has a smooth, flat, horizontal surface. In addition, the cross member is connected to the side legs by internal angular sections. For one of its applications, the staple is used as an osteosynthesis device and, consequently, it is intended to be sunk into the bone in such a way that its cross member bears on the bone in the region of the fracture.

This staple clearly has a number of disadvantages for osteosynthesis, notably that, once it is in place, the staple tends to spread by reaction and consequently produce an opposite effect to that desired, which is to draw together and anchor the bone fragments to be fused. In fact, the sharpened section of each of the side legs of the staple has a point directed towards the interior which has the effect of forcing the legs towards the interior when penetrating the bone and thus causing an outwards reaction by elastic restitution. This reaction will in practice tend to separate the bone fragments. It should be noted that the arrangement of the series of teeth on the external surfaces of the side legs reinforces this separating effect by reaction. Also, if the staple does not have any additional fixing devices, it will be displaced not only by the progressive formation of callus (bony substance produced in the outer part of the bone which progressively fuses the bone fragments together) around the side legs, but also by the effect of the aforesaid reaction which naturally tends to eject it from the bone.

There is another bone surgery staple as described in Swiss patent CH-A-597 839. In this version the sharpened ends of the legs are such that the sloping surfaces forming the bevels face each other, which is a considerable advantage over the previous staple. However, once implanted, this staple does not provide any elastic compression of the bone fragments.

Moreover, none of the earlier designs takes account of the bone structure into which the staples are to be implanted. In particular, there is no mention in the previous documents of the fundamental differentiation between the very hard and brittle cortical bone and the somewhat soft and spongy metaphysis. Staples frequently have to be implanted lengthways in the bone, that is one leg in the metaphysis and the other in the cortical bone. This is notably the case for knee articulation surgery.

Another problem is that the cross member of such staples has a smooth, perfectly flat and horizontal internal surface. This geometry does not allow the internal surface of the cross member of the staples to mate properly with the generally concave surface of long bones which, apart from anything else, could have regions of discontinuity resulting notably from an osteotomy with derotation of the bone fragments.

Even when perfectly inserted into the bone, this type of staple always has an area which is not in contact with the bone. This failure to make contact is particularly serious for osteosynthesis: initially, it causes mechanical weakness and, additionally, the callus that will develop in the interstices will cause pressure on the staple which will be progressively displaced. This inevitably leads to a new operation with the undesirable consequences that can be imagined.

Finally there is another anterior patent U.S. Pat. No. 4,848,328 which descries an osteosynthesis staple whose side legs may be slightly divergent and whose ends are also provided with bevels, the sloping surfaces of which face each other for good reasons. This staple, for which a stepped variant is also described, is difficult to fit the shape of long bones and risks, in the same way as the previous solutions, being easily displaced. Finally, it is clear that this model of staple does not take account of the different natures of the bone into which the legs penetrate depending on whether the operation takes place in the metaphysis or the cortical bone.

SUMMARY OF THE INVENTION

The present invention aims to remedy all these problems, by describing a plate-staple which may be perfectly anchored in the bone, providing a notable, dynamic clamping of the bone fragments on either side of the fracture line, and moreover without any particular difficulty in handling or implantation.

According to the invention, the osteosynthesis plate-staple incorporating side legs having sharpened free ends provided with anti-return elements, the legs being joined by a cross-member, is characterized by the side legs having different configurations and longitudinal directions noticeably divergent from each other and by the cross member having on at least one part of its length and at least on the interior surface a profile convex on the inside of the staple. It also has provision for additional fixings to pass through it via holes drilled in said cross member.

According to one particular, essential variant, the plate-staple is moreover designed so that its side legs are of different forms depending on whether they are intended to penetrate the metaphysis or to be implanted in the cortical bone.

Moreover, according to another notable characteristic of the invention, the cross member of the staple has an internal surface which is specially rough or even porous to encourage the development of microvascularisation and consequent formation of cortical callus. Moreover, a sufficiently porous retentive surface of this type could be additionally coated with hydroxyapatite whose qualities are well known in the field of bone repair.

Moreover, if the plate-staple is particularly intended for osteotomy of the lower limbs, that is of the long bones, it is therefore naturally implanted along the longitudinal is of the bone. Given that it is well known that such bones have concave lateral surfaces along their length, provision has been made to profile the cross member of the staple convexly so that it is better able to mate with the surface of the bone with the fortuitous advantage of adding to the lateral elasticity of the legs, which further reinforces the automatic clamping effect of the bone fragments on either side of the fracture line. Furthermore, for this purpose two types of osteotomy staples have been chosen:

one for osteotomies without discontinuity of the bone fragments and, in this case, the cross member of the staple is continuous and is convex on the internal surface of the staple, the other for osteotomies with partial or total derotation of the bone fragments creating a discontinuity in the external lateral surface of the bone. In this case, the cross member of the staple is discontinuous in the general form of steps, each part of the cross member nevertheless showing a convexity better suited to mating with the bone surface.

In accordance with a further characteristic of the invention, the side legs of the plate-staple are joined to the cross-member by internal and external attachment zones suitably curved to obtain greater elasticity of the side legs and more generally of the structure of the plate-staple as a whole.

In accordance with a secondary characteristic of the invention, the side legs have, firstly, on their internal surface, a series of teeth the ridges of which point towards the inside of the cross member and, secondly, at the end of the inner surface of each of the two legs, a bevel whose sloping surfaces face each other. This forces the legs apart from each other during implantation of the plate-staple. During implantation, the side legs of the plate-staple are thus subject to an elastic outward force which produces the desirable inward force by the legs, thus anchoring the bone fragments that are to be fused.

According to a final general characteristic of the invention, the cross member has two holes drilled on either end of an axis passing vertically through the center of the cross member of the plate-staple. The axis of each hole is approximately parallel to the nearer side leg. The holes being intended to take additional fixing elements, such as screws, giving the plate-staple a double role as staple and osteosynthesis plate, thus providing greater immobilization of the bone fragments to be fused.

BRIEF DESCRIPTION OF THE DRAWINGS

Other characteristics and advantages will become more evident from the following description of several preferred variants of the application of the present invention, given as non-limiting examples.

FIG. 1 shows a perspective view of the plate-staple according to a first embodiment of the present invention, particularly suited to osteotomies without derotation of the bone fragments, FIG. 1A shows an enlarged view of the holes for receiving fixing elements.

FIG. 1B shows an enlarged view of the tips of one side leg illustrating an enlarged view of the bevel.

FIG. 2 is a perspective view embodiment of the plate-staple according to the second of the present invention, particularly suited to osteotomies with derotation of the bone fragments.

FIGS. 3a, 3b and 3c are successive schematic cross-sections of any staple with divergent legs whose ends have bevels facing each other, showing firstly the stages of implanting a plate-staple in accordance with the invention, and secondly, showing the stages of the relative movement of the side legs during their implantation.

DETAILED DESCRIPTION OF THE PREFERRED EMBODIMENTS

According to FIG. 1, the variant of the plate-staple has two side legs, 1 whose longitudinal directions are noticeably divergent from each other towards their ends and connected by a specially profiled cross member 2 to mate exactly with the external surface of the bone. The convex profile of the cross member 2 of the staple facing towards the interior of the latter is derived from the average value of the concavity of the lateral surface of the long bone that is to be treated. As a non-limiting example, for a staple with opening of 37 mm, the radius of curvature of the cross member 2 is close to 90 min.

It is therefore very clear that the profile of the cross member 2 could be derived as a variant of the invention simply by thickening the internal surface of the cross member 2. The external surface could then have any profile.

Figure 4:
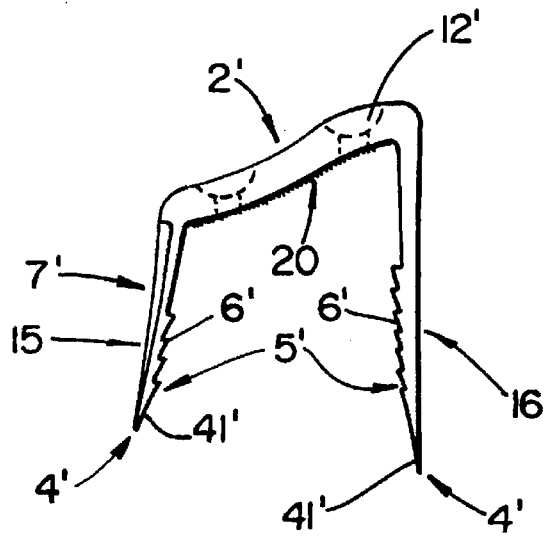
FIG. 4 is an elevational view of the asymmetric plate-staple according to the invention particularly suited to tibial osteotomy with derotation of the bone fragments.
Figure 5:
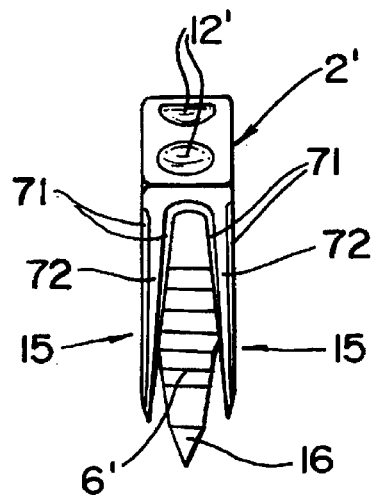
FIG. 5 is a left view of the preceding embodiment of the staple.
Figure 6:
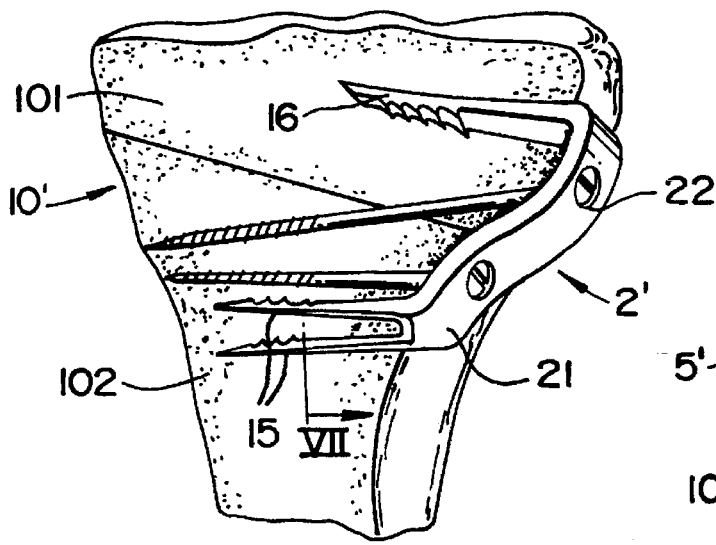
FIG. 6 is a perspective view of the plate-staple according to the embodiment shown in FIGS. 4 and 5.

The side legs 1 of the plate-staple have a straight section that is approximately rectangular and that narrows evenly from the junction 3,3' with the cross member 2,2' up to their sharpened ends 4,4'. As illustrated, for example, in FIGS. 1B and 4, the end 4,4' of each leg 1 is bevelled from the inside towards the outside in such a way that the sloping surface 41,41' of one leg faces the sloping surface of the other. In addition, the internal surfaces 5,5' of the side legs 1 have anti-return elements, preferably a series of teeth 6,6' arranged as a rack with the points facing the opposite way to the direction of penetration into the bone during implantation. The particular direction of the side legs 1, the orientation of the bevel at the end 4,4' from the interior to the exterior, as well as the arrangement of the teeth 6,6', tend to cause the side legs 1 to spread during the implantation of the plate-staple. This has the effect of producing a positive reaction towards the interior of the side legs 1 as a result of the implantation. The teeth 6,6' provide the staple with a stable anchor within the bone and prevent the side legs 1 from coming free.

The internal surfaces 5,5', as well as the external surfaces 7,7', of the side legs 1 are connected respectively to the cross member 2,2' by internal zones 8,8' and external zones 9,9' that are specially rounded. This suitably rounded form gives the structure of the plate-staple its flexibility and above all its elasticity necessary for implantation in the bone.

The internal surface 20,20' of the cross member 2,2' has a knurled finish obtained, for example, by moulding or else diamond cutting at 300 microns, which in addition to its specially profiled shape allows the best possible contact with the surface of the bone 10,10' into which the plate-staple is implanted. The roughness of the surface complements the porosity of the metal preferably used for manufacturing the staple. This helps the development of microvascularization at the edge of the bone fragments and therefore faster development of cortical callus as already described. The relatively large area of the contact surface 20,20' of the cross member 2,2' enables good osteosyntheses to be achieved because the bone fragments 10,10' are held in place, a process which is all the more effective because they are pressed together. The bone fragments 10,10' are held in place securely by two additional fixing elements 11,11', for example screws, which go onto either end of the cross member 2,2' through holes 12,12' drilled in the cross member 2,2'. According to one particular characteristic, the general direction of the axis of each of the holes 12,12' is approximately parallel to that of the nearest side leg 1. In addition, the holes 12,12' are located symmetrically either side of the vertical axis y,y', shown in FIGS. 3a and 3b passing through the center of the cross member 2 in the median plane of the staple. According to another complementary characteristic, each of the holes 12,12' on the upper section of the cross member 2,2'has a recess for the screw head 11,11' that is in the form of a cylindro-hemisphere, type D2 of the French standard NF S 90-410, to allow a certain axial freedom to the screws 11,11' when they are being implanted in the bone fragments.

In the particular design shown in FIGS. 1, 3a, 3b and 3c, the height of the staple is approximately equal to its width. The cross member 2 is specially profiled, the profile being curved towards the inside of the plate-staple along the axis y,y'. In addition, as shown therein, the side legs and the cross ember are unitary, i.e., they are made from a single piece of material.

In the particular design shown in FIG. 2, the height of the staple is noticeably greater than its width. Seen from the front, the cross member 2' has the general form of a step facing from side leg 13 towards the other side leg 14. One of the two side legs 14 is longer than the other 13, which gives the staple the general appearance of a stepped staple. This stepped shape enables the internal surface 20' of the cross member 2' of the plate-staple to mate as well as possible with any bone surface that has a discontinuity either natural or artificial, notably for osteotomy with derotation of the bone fragments. Naturally, this internal surface 20' also has a roughened surface obtained as in the preceding embodiment, by knurling or diamond cutting. Moreover, for the same reasons already mentioned for the preceding embodiment, the lower step 21 of the cross member 2' near to the small side leg 13, intended to bear on the lateral concave surface of the bone, is convex as for the preceding staple, whereas the upper step 22 of the cross member 2' near to the long leg 14 is concave in shape, preferably with the same radius of curvature as that of the convex part 21, to mate as well as possible with the displaced bone fragment. More specifically, it can be seen that, in either embodiment, the lowermost surface of the cross member immediately adjacent one of the side legs is convex.

Steps 21 and 22 are of course preferably the same width, although this is not however essential, and it is clear that any variant in shape, for example, a stepped staple whose upper step 22 is flat in conjunction with a lower convex step 21 would not fall outside the scope of the invention.

In relation to FIGS. 4, 5, 6 and 7 several designs of the plate-staple according to the invention are described in order to take account of the particular bone structure into which each leg of the staple may be implanted during osteotomy. It should be remembered in this respect that the metaphysis of the long bones is soft and spongy whereas the cortical part of the bone is very hard and brittle.

For this reason, notably for knee joint surgery, a particular application of the invention is proposed according to which the type of plate-staple just described also has a new and important characteristic in that its side legs 15,16 are shaped differently depending on whether they are intended to penetrate the metaphysis 101 of the bone 10' or to be implanted in the cortical bone 102. In addition to all the characterized detailed hereinbefore, this type of staple is characterised by having leg 16, shaped for the metaphysis 101, comprised of a plate of approximately constant thickness starting at one end of the cross member 2' of the staple, the same width at its base as the member 2', extending and narrowing progressively to form a tip 4' that is sharpened at left and right in addition to the bevel 41' explained in detail hereinbefore, and by having the other leg 15 comprising at least one finger coming from the other end of the cross member 2', extending in a direction noticeably divergent from the direction of the metaphysis leg 16, the straight section of the finger having a cross-section allowing it to be implanted into a cavity in the cortical bone 102 formed by a pilot hole 100 with a smaller section.

Figure 7:
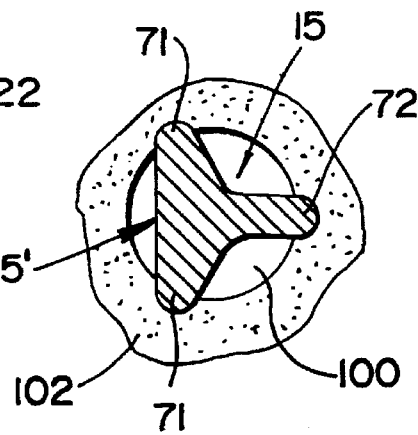
FIG. 7 is a partial section along the axis VII of FIG. 6, of the cortical leg of an asymmetric staple according to the invention represented in FIGS. 4 and 5.

In relation to FIG. 7, it should be noted that one of the cross-sections best adapted to the cortical leg 15 is formed of three rounded ridges 71,72 which may be drawn within an equilateral triangle of which one side corresponds to the approximately flat internal part 5,5' of leg 15 and the opposite apex to a longitudinal ridge 72, stiffening the external part 7' of said leg 15, the two other apexes corresponding to the lateral edges 71 of the same leg 15.

With this form, leg 15 of the asymmetric staple can be implanted through a pilot hole 100 drilled in the cortical part of the bone 102, without risk that the implantation will cause the hard, brittle cortical part of the bone to shatter, as frequently happens with the normal type of staple. Equally, an additional advantage of this embodiment of staple is that the ridges 71 and 72 emerging from the straight part of the leg 15 are rounded, which again avoids risk of the cortical part of the bone shattering during implantation.

It is evident that it may be advisable to provide leg 15 with several fingers whose straight part has the cross section that has just been described. More particularly, there may be two fingers arranged in the plane of leg 15 so as to provide the staple with greater general stability, notably with respect to rotation. It is also very useful to arrange that the two fingers forming leg 15 have, themselves, a certain longitudinal divergence in order to benefit from a certain amount of elasticity that is very advantageous to the general stability of the implanted staple.

It is very clear that legs 15 and 16 as have just been described can be used with a bowed plate-staple of the type shown in FIG. 1, in the same way as they can be used with the stepped staples as shown in FIGS. 2 and 4 to 7.

It can be noted that the stepped staple of FIG. 2 has a distinct transition portion 23 between the lower and upper steps 21, 22, whereas the lower and upper steps in the staple of FIGS. 4–7 are immediately adjacent, or essentially immediately adjacent, i.e., without or essentially without, a transition portion therebetween.

All the additional and secondary characteristics which were described at length for the staple shown in FIG. 1 are of course applicable to the stepped staples, that is the existence of anti-return elements 6,6' on the side legs 15 or 16, additional fixing elements such as screws 11 in the cylindro-hemispheric rebates 12', or again the special surface treatment that can be applied to the internal surface 20 of the cross member 2 or 2' of the plate-staple according to the invention.

FIGS. 3a, 3b and 3c demonstrate in a very schematic form the characteristic effect of the invention taking as example the plate-staple in FIG. 1 during the phases of its implantation in the bone 10. It is clear that, once they have been implanted, the side legs 1 of the plate-staple which have been subjected to an elastic spreading during implantation, then react in the opposite direction, which tends to prestress the bone fragments on either side of the fracture line.

The plate-staples according to all embodiments of the invention are made preferably by moulding using titanium or chrome-molybdenum-cobalt alloys, biologically compatible materials with suitable mechanical properties for the applications described.

We claim:

1. Osteosynthesis plate-staple intended to produce by elastic reaction a compression of bone fragments on either side of a fracture line, said plate-staple comprising:

side legs comprising free sharpened ends and anti-return elements, said side legs having different configurations with respect to each other and extending in longitudinal directions divergent from each other;

a cross member joining said side legs, said cross member comprising a length and an interior surface, and a convex profile on at least about a half of said length and said interior surface; and openings in said cross member permitting additional fixings to pass through said openings.

2. The plate-staple according to claim 1, wherein one of said side legs has a shape adapted to penetrate the metaphysis of a bone, and another of said side legs has a shape adapted to be implanted in a cortical bone.

3. The plate-staple according to claim 2, wherein:

said cross member comprises a width, and first and second ends;

said one of said side legs having a shape adapted to penetrate the metaphysis of a bone comprises a plate of substantially constant thickness, said plate comprising a first end at said first end of said cross member, said first end of said plate having a same width as said width of said cross member, and said plate extending in a first direction from said cross member and progressively narrowing to form a sharpened tip; and said another of said side legs having a shape adapted to be implanted in a cortical bone comprises at least one finger protruding from said second end of said cross member, and extending in a second direction different from said first direction, and said finger comprising a straight section comprising a cross-section enabling implantation into a cavity in the cortical bone formed by a pilot hole with a smaller section.

4. The plate-staple according to claim 3, wherein said at least one finger comprises a cross-section formed of three rounded ridges positioned in an equilateral triangle including one side substantially corresponding to a flat internal part of said at least one finger, and an apex of said equilateral triangle opposite said one side substantially corresponding to a longitudinal ridge stiffening an external part of said leg, with the remaining two apexes corresponding to lateral edges of said at least one finger.

5. The plate-staple according to claim 3, wherein said at least one finger comprises two fingers protruding from said cross member, said two fingers extending in planes that are parallel to a plane passing through said one of said side legs and said internal surface of said cross member, and said two fingers extending in longitudinal directions that are divergent.

6. The plate-staple according to claim 5, wherein each of said two fingers comprise a cross-section formed of three rounded ridges positioned in an equilateral triangle including one side substantially corresponding to a flat internal part of said each finger, and an apex of said equilateral triangle opposite said one side substantially corresponding to a longitudinal ridge stiffening an external part of said leg, with the remaining two apexes corresponding to lateral edges of each said finger.

7. The plate-staple according to claim 5, wherein said cross member is stepped-shaped, and comprises a lower step comprising a convex internal surface and an upper step comprising a concave internal surface.

8. The plate-staple according to claim 5, wherein said cross member is stepped-shaped, and comprises a lower step comprising a convex internal surface and an upper step comprising a flat internal surface.

9. The plate-staple according to claim 1, wherein each of said side legs comprises an end spaced from said cross member and an internal surface, and further comprising a bevel on each of said side legs, each said bevel being positioned on said internal surface and at said end of a side leg, and comprising a sloping surface facing a bevel on a corresponding side leg.

10. The plate-staple according to claim 1, wherein said interior surface of said cross member comprises an internal surface that is sufficiently rough to assist development of microvascularization between the staple and the bone.

11. The plate-staple according to claim 10, wherein said internal surface of said cross member comprises a knurled or diamond cut finish.

12. The plate-staple according to claim 1, wherein said interior surface of said cross member comprises an internal surface that is sufficiently rough and retentive to receive a coat of hydroxyapatite before implantation.

13. The plate-staple according to claim 12, including a coat of hydroxyapatite on said internal surface.

14. The plate-staple according to claim 1, wherein said side legs comprise an interior surface, and said anti-return elements are positioned on said interior surface of said side legs.

15. The plate-staple according to claim 14, wherein said anti-return elements comprise inwardly pointing ridges.

16. The plate-staple according to claim 1, wherein said side legs comprise an interior surface and an exterior surface, and said side legs are connected to said cross member by rounded internal and external zones.

17. The plate-staple according to claim 1, wherein each of said openings comprises a recess having a shape adapted to receive a head of a fixing element in a general form of a cylindro-hemisphere.

18. The plate-staple according to claim 1, wherein said cross member is step-shaped, and comprises a lower step comprising a convex internal surface about half the length of said cross member and an upper step comprising a concave internal surface about half the length of said cross member.

19. The plate-staple according to claim 1, wherein said cross member is step-shaped, and comprises a lower step comprising a convex internal surface about half the length of said cross member and an upper step comprising a flat internal surface.

20. The plate-staple according to claim 18 wherein said lower step and said upper step have widths different with respect to each other.

21. The plate-staple according to claim 1, wherein said side legs comprise an interior surface, and said anti-return elements are positioned on said interior surface of said side legs.

22. The plate-staple according to claim 19, wherein said lower step and said upper step have widths different with respect to each other.

23. The plate-staple according to claim 1, wherein said side legs and said cross member are unitary.

24. The plate-staple according to claim 1, wherein said one portion of said length and interior surface of said cross member is a lowermost length and surface of said cross member, and wherein said lowermost length and surface extends immediately from one of said side legs.

25. The plate-staple according to claim 1, wherein said cross member comprises a lower step and an upper step, said lower step constituting said portion of said length of said cross member having said convex profile.

26. The plate-staple according to claim 25, wherein said convex profile of said lower step extends immediately from one of said side legs.

27. The plate-staple according to claim 25, wherein said cross member further comprises a transition portion between said lower step and said upper step.

28. The plate-staple according to claim 25, wherein said lower step is immediately adjacent to said upper step.

29. An osteosynthesis staple intended to produce by elastic reaction a compression of bone fragments on either side of a fracture line, said staple comprising:

side legs having shapes that differ with respect to each other and extending in longitudinal directions divergent from each other, each said side leg having anti-return elements on a surface facing the other said side leg, and each said side leg having a bevelled end comprising a bevel surface facing the other said side leg;

a cross member joining said side legs, said cross member comprising a length and an interior surface, and a convex profile on at least about a half of said length and said interior surface; and openings in said cross member permitting additional fixings to pass through said openings.

30. The plate-staple according to claim 29 wherein said side legs and said cross member are unitary.

31. The plate-staple according to claim 29, wherein said one portion of said length and interior surface of said cross member is a lowermost length and surface of said cross member, and wherein said lowermost length and surface extends immediately from one of said side legs.

* * * * *